United States Patent [19]

Clemente et al.

[11] Patent Number: 5,576,346
[45] Date of Patent: Nov. 19, 1996

[54] PROCESS FOR TREATING UREMIC PRURITUS

[75] Inventors: Emmett Clemente, Manchester; Robert W. Mendes, Dedham; Aloysius O. Anaebonam, Burlington; Mumtaz Ahmed, Westford, all of Mass.

[73] Assignee: Ascent Pharmaceuticals, Inc., Billerica, Mass.

[21] Appl. No.: 415,718

[22] Filed: Apr. 3, 1995

[51] Int. Cl.$^6$ ............................................. A61K 31/35
[52] U.S. Cl. ...................................................... 514/456
[58] Field of Search ............................................. 514/456

[56] References Cited

U.S. PATENT DOCUMENTS

| | | | |
|---|---|---|---|
| 4,271,182 | 6/1981 | Sullivan | 514/456 |
| 4,362,742 | 12/1982 | Sullivan | 514/456 |

FOREIGN PATENT DOCUMENTS 0587264  3/1994  European Pat. Off. .

OTHER PUBLICATIONS

Chemical Abstracts, vol. 87, No. 26, "Topical Compositions for Skin Diseases", Brit. 1,475,503 (1978).
Habif, T. P., ed., Clinical Dermatology: A Color Guide to Diagnosis and Therapy, 2nd Ed., The C. V. Mosby Co. (St. Louis MO: 1989) pp. 582–585.
Brauenwald, et al., eds., Harrison's Principles of Internal Medicine, 11th Ed., McGraw–Hill Book Co. (New York: 1990), pp. 3043, 1161, and 1958.

*Primary Examiner*—Kevin E. Weddington
*Attorney, Agent, or Firm*—Welsh & Katz, Ltd.

[57] ABSTRACT

A process and pharmaceutical composition for treatment of uremic pruritus in humans is disclosed. The pharmaceutical composition comprises of a chromone compound of the following formula, or a pharmacologically acceptable salt, ester or amide thereof:

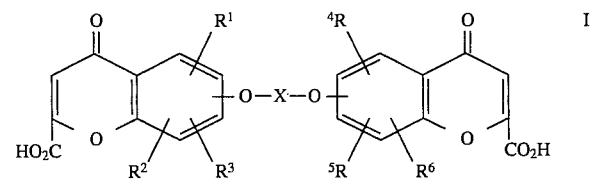

dissolved or dispersed in a pharmacologically acceptable carrier. In accordance with the process, a therapeutically effective amount of the composition is topically administered to a pruritic lesion of a human patient.

11 Claims, No Drawings

PROCESS FOR TREATING UREMIC PRURITUS

DESCRIPTION

1. Technical Field

This invention relates to the treatment of uremic pruritus, and more particularly to a composition and process for treating uremic pruritus that utilizes a chromone compound of the general formula shown in formula I, hereinafter, wherein $R^1$, $R^2$, $R^3$, $R^4$, $R^5$ and $R^6$ i.e. $R^1$–$R^6$ and X are defined hereinafter.

2. Background of the Invention

A Compound of formula I, hereinafter, and its pharmacologically acceptable salts, esters and amides has been used successfully in the treatment of asthma for many years. One particular compound, commonly known as cromolyn, is routinely used as a prophylatic treatment for asthma, rhinitis, conjunctivitis and intestinal mastocytosis.

Cromolyn is not a bronchial or vasodilator as is usual for asthma treatments. Rather, cromolyn acts to inhibit the release of inflammatory mediators such as histamine from several types of cells. Inhalation of a solution containing the disodium salt of cromolyn, (cromolyn sodium), on a regular schedule by an individual suffering from asthma provides a prophylatic treatment for bronchial asthma. The prophylatic response increases with the length of use of the drug.

A chromone compound corresponding to formula I and its pharmacologically acceptable salts, esters and amides has also been reported to be effective against certain allergic skin disorders such as atopic eczema and various skin conditions that involve skin mast cells and/or an antibody-antigen reaction. (Sullivan U.S. Pat. Nos. 4,362,742 and 4,271,182), as well as being affective against allergic conditions of the eye. However, the effectiveness of these compounds against other conditions of the skin or epidermis is not predictable.

The exact mechanism of action of a chromone compound is unknown. A chromone compound is believed to possess no vasodilator, antihistaminic or anti-inflammatory activity. It is known that a chromone compound, and particularly cromolyn, is poorly absorbed by the lungs and by the gastrointestinal tract. Only about 7–8 percent of a usual total dose is absorbed from the lung, and is then rapidly excreted, unchanged, in the bile or urine. The remainder is expelled from the nose or, if swallowed, excreted by the alimentary tract.

Uremic pruritus is a disease of unknown cause that arises in patients with end stage renal failure. The disease afflicts up to 86 percent of patients undergoing maintenance hemodialysis. [Young et al., *N.Y. State J. Med.*, 73:2670–2674 (1973); Bencini et al., *Nephron*, 40:316–320 (1985); Gilcrest et al., *Arch. Dermatol.*, 118:154–156 (1982); Young et al., *Arch. Dermatol.*, 109:107)1974); Rosen, in *Cutis.*, 23:790–792 (1979)]. Proposed etiologies include dermal xerosis, peripheral neuropathy, vitamin A intoxication, secondary hyperparathyroidism, dystrophic dermal calcification, and azotemia associate mast cell proliferation and degranulation. [Nielsen et al., *Dan. Med. Bull.*, 27:269–271 (1980); Massry et al., *N. Engl. J. Med.*, 279:697–700 (1968); Raskin et al., *N. Eng. J. Med.*, 294:204–210 (1976); Yatzidis et al., *Br. Med. J.*, 3:352–353 (1975); Stockenhuber et al., *N. Eng. J. Med.*, 317:386 (1987); Stockenhuber et al., *Clin. Sci.*, 79:477–482 (1990)].

Yago et al., *Nippon Jinzo Gakki Shi*, 31:1061–1067 (1989) measured C3a, C5a, bradykinin and lipid peroxide in the venous blood collected before dialysis from patients with chronic renal failure. They discovered that the C3a levels increased considerably in prurutic patients compared to nonpruritic patients within 15 minutes after starting hemodialysis. Neurotropin, an analgeic and antiallergic drug marketed in Japan significantly suppressed the C3a level and improved the condition of pruritic patients. Bradykinin levels were not significantly different between the two groups. Lipid peroxides were also somewhat decreased by neurotropin. Those authors concluded that neurotropin exerts its antipruritic effect through suppression of the activation of C3 in patients undergoing hemoldiaylsis.

Bergasa et al., *Life Sci.*, 53:1253–1257 (1973) observed that the extracts of plasma samples from patients with the pruritus of cholestasis induced facial scratching when injected into the medullary dorsal horn of monkeys. This effect could be abolished with naloxone, an opioid receptor antagonist. The plasma from nonpruritic patients was unable to induce facial scratching. The authors concluded that the pruritus of cholestasis appeared to be due to a central opioid receptor-mediated mechanism.

Although uremic pruritus is not itself life-threatening, the itching caused can be quite severe and disagreeable to patients already suffering from renal failure. It would therefore be advantageous to be able to successfully treat uremic pruritus lesions without adverse side effects. The disclosure that follows provides one such treatment.

SUMMARY OF THE INVENTION

A process for treating uremic pruritus is disclosed herein. This process utilizes topical administration of a formulation containing a lesion-reducing amount of a compound of formula I, or a pharmacologically acceptable salt, ester or amide thereof. The particularly preferred compound is commonly referred to as cromolyn [1,3-bis(2-carboxychromon-5-yloxy)-2-hydroxypropane] and is represented in formula II, hereinafter.

Surprisingly, it is found that topical treatment with cromolyn reduces the inflammation of the underlying vessels, causing the lesion to regress thereby eliminating the discoloration of the skin caused by the uremic pruritus. This process of treatment results in early regression of the lesion with no known side effects. It can therefore be used on a great number of lesions, not merely those threatening harm to the patient.

The compound utilized in the present process as the active agent and hereinafter referred to as the "active agent" or "active ingredient", in the treatment conforms to the structure of formula I, below, and includes pharmacologically acceptable salts, esters and amides thereof where $R^1$, $R^2$, $R^3$, $R^4$, $R^5$ and $R^6$; i.e. $R^1$–$R^6$ and X are further defined herein and X are further defined hereinafter.

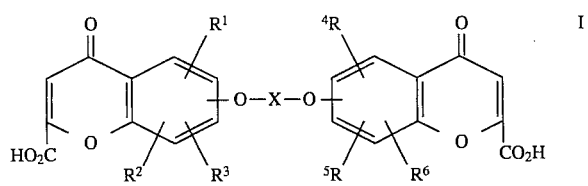

The molecule of formula I can be generally described as two chromone molecules linked by an O—X—O chain. In the above formula, and in all other formulas shown herein, hydrogen atoms that are not needed to show conformation about a particular bond are not shown.

Although $R^1$–$R^6$ can vary as fully described hereinafter, in general, it is preferred that no more than one of $R^1$, $R^2$ and $R^3$ and no more than one of $R^4$, $R^5$ and $R^6$ is other than hydrogen, and each is selected from a hydrogen, a halogen atom, a $C_1$–$C_6$ alkyl, hydroxy, $C_1$–$C_6$ alkoxy or substituted alkoxy group, and X is as defined hereinafter. More preferred compounds of formula I are those in which each of $R^1$–$R^6$ is hydrogen, and the carboxyl groups are present as alkali metal carboxylate salts.

The X group is preferably a straight or branched hydrocarbon chain containing 3 to 7 carbon atoms. The chain can be interrupted by one or more oxygen atoms. Even more preferably the chain is a polymethylene chain substituted by one or more hydroxyl groups, with a 2-hydroxy-trimethylene chain (—$CH_2CHOHCH_2$—) being a particularly preferred chain.

Although the above describes more preferred X groups, X can be one of a wide variety of groups as fully set forth hereinafter.

The structure of a particularly preferred compound of formula I is shown below as formula II, and is commonly known as cromolyn:

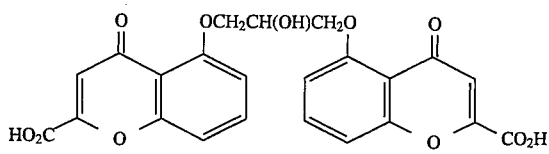

The most preferred derivative of formula II for use in the disclosed process is the disodium salt thereof, hereinafter referred to as cromolyn sodium.

A contemplated process comprises the administration to a human with uremic pruritus of a composition that contains a pharmacologically acceptable carrier having dissolved or dispersed therein a therapeutically effective (lesion-reducing) amount of a compound of formula I or a pharmacologically acceptable salt, ester or amide thereof, as an active ingredient or agent. That composition is topically applied to the pruritic (itchy) area of the skin. The composition can be applied to the lesion several times a day and then either be covered or left open to the air. Exemplary therapeutically effective amounts, by weight, of the active ingredient can range from about 0.5 to about 10 percent of the total composition.

The present invention has several benefits and advantages.

One benefit is that use of the described process and composition can reduce or eliminate the lesions on the skin caused by uremic pruritus without adverse side effects.

One advantage of the described process is that it can be used for most uremic pruritus lesions causing early regression of the lesion even where there is no immediate physical harm being caused or threatened.

Further benefits and advantages of the invention will be apparent to those of skill in the art from the description that follows.

DETAILED DESCRIPTION OF THE INVENTION

The present invention contemplates a process for treatment of uremic pruritus. A contemplated process utilizes a compound corresponding to formula I, preferably the compound commonly known as cromolyn, (formula II) and more preferably the disodium salt of cromolyn, as an active agent compound in a composition that is topically administered to the uremic pruritus lesions of humans in need of such treatment; i.e., having uremic pruritus.

A. Compounds

A compound utilized in the present invention is represented by formula I.

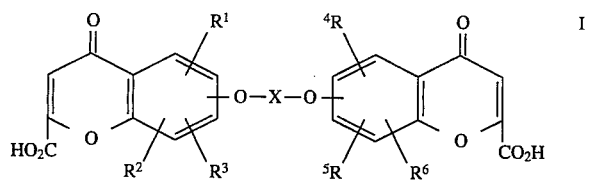

Each of $R^1$–$R^6$ can be the same, or different. Each $R^1$–$R^6$ can be a hydrogen; a halogen (halo) group or moiety (i.e. chloride, bromide, iodide or fluoride); a $C_1$–$C_6$ lower alkyl group (i.e. a methyl, ethyl, propyl, isopropyl, butyl, tertiary-butyl, or hexyl group); hydroxy; $C_1$–$C_6$ lower alkoxy (i.e. a methoxy, ethoxy, propoxy, isopropoxy, butoxy, tertiary-butoxy or hexyloxy group); substituted $C_1$–$C_6$ lower alkoxy group; or a substituted $C_1$–$C_6$ lower alkyl, as are discussed below.

The substituted lower alkyl or alkoxy group can be substituted with the following groups: hydroxyl; lower ($C_1$–$C_6$) alkoxy; carboxy or halo such as chloro-bromo-iodo- or fluoro-); $C_1$–$C_6$ lower alkenyl, e.g. allyl or methyl-allyl; benzyl; and nitro. A substituent group is not itself substituted. It is preferred that each $R^1$–$R^6$ be unsubstituted.

In general, it is preferred that no more than one of $R^1$, $R^2$ and $R^3$ and no more than one of $R^4$, $R^5$ and $R^6$ is other than hydrogen, and each is selected from a hydrogen, a halogen atom, a $C_1$–$C_6$ alkyl, hydroxy, $C_1$–$C_6$ alkoxy or substituted alkoxy group, and X is as defined before. A preferred compound is symmetric with $R^1$ being the same as $R^4$, $R^3$ being the same as $R^5$ and $R^2$ being the same as $R^6$. More preferred compounds of formula I are those in which each of $R^1$–$R^6$ is hydrogen.

The bridging X group of formula I is a saturated or unsaturated, substituted or unsubstituted, straight or branched polymethylene chain having between 3 and 10 carbon atoms can be interrupted by one or more carbocyclic rings or oxygen-containing heterocyclic rings, (e.g. benzene, dioxan, tetrahydrofuran, or dihydropyran rings), oxygen atoms or carbonyl groups.

The X group is preferably a straight or branched hydrocarbon chain containing 3 to 7 carbon atoms. The chain can be interrupted by one or more oxygen atoms. Even more preferably, the chain is a polymethylene chain substituted by one or more hydroxyl groups, with a 2-hydroxy-trimethylene chain (—$CH_2CHOHCH_2$—) being a particularly preferred chain. The structure of a particularly preferred compound of formula I is shown below as formula II, and is commonly known as cromolyn:

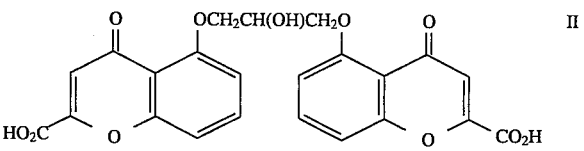

Although the above describes more preferred X groups, X can be one of a wide variety of groups as set forth hereinafter.

The X group can be a straight or branched, saturated or unsaturated hydrocarbon chain. Additionally, X can be such a chain interrupted by one or more oxygen atoms, carbonyl groups or carbocyclic or heterocyclic rings and can be substituted by one or more halogen atoms (e.g. chlorine, bromine, iodine or fluorine atoms), or hydroxy or $C_1$–$C_6$ lower alkoxy (e.g. methoxy, ethoxy, propoxy, isopropoxy, butoxy, tertiary-butoxy, etc.) groups. Some specific examples of the X group are groups of the following formulas:

—(CH$_2$)$_5$—
—CH$_2$—CH=CH—CH$_2$—
—CH$_2$CH$_2$CH—(CH$_3$)—CH$_2$CH$_2$—
—CH$_2$CH$_2$OCH$_2$CH$_2$—
—CH$_2$COCH$_2$—
—CH$_2$CH(OC$_2$H$_5$)—CH$_2$—
—CH$_2$CHOHCH$_2$—
—CH$_2$CHOHCH$_2$OCH$_2$CHOHCH$_2$—

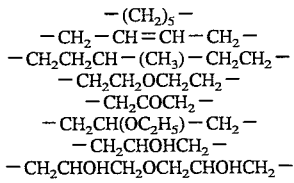

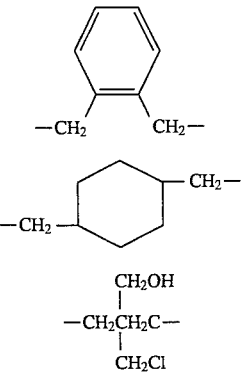

Different or corresponding positions on the chromone molecules can be linked by the O—X—O chain, although symmetrical linkages are preferred.

Pharmacologically acceptable salts of a compound of formula I or formula II suitable for use in the disclosed process include for example, ammonium salts, alkali metal salts (e.g. sodium, potassium and lithium), alkaline earth metal salts (e.g. magnesium and calcium), and salts with organic amines (e.g. mono-, di- or tri-$C_1$-$C_6$-alkyl amines, piperidine, morpholine and trialkanol $C_1$-$C_6$-alkyl amine salts).

Pharmacologically acceptable esters include simple $C_1$-$C_6$ alkyl esters (e.g. methyl, ethyl, propyl, isopropyl, butyl, tertiary-butyl and hexyl esters). Pharmacologically acceptable amides include simple amides (for example amides with ammonia and $C_1$-$C_6$ lower alkylamines such as methylamine, ethylamine, and the like whose alkyl portions are discussed before) and more complex amides with amino acids, e.g. glycine.

Specific examples of compounds of formula I and derivatives thereof are provided in U.S. Pat. No. 4,362,742, whose disclosures are incorporated herein by reference.

The most preferred derivative of formula II for use in the disclosed process is the disodium salt thereof, hereinafter referred to as cromolyn sodium.

The phrase "pharmacologically acceptable" salts, esters and amides as used herein refers to non-toxic salts, esters and amides of formula I as discussed above.

B. Compositions

The compound of formula I or one of its pharmacologically acceptable salts, esters or amides dissolved or dispersed in a therapeutically effective amount in a pharmacologically acceptable carrier constitutes a composition (preparation) useful in a process of this invention. The disodium salt of a compound of formula II, where $R^1=R^2=R^3=R^4=R^5=R^6=H$, and X=—CH$_2$CHOHC$_2$H—, is preferred for use in treatment.

Although a compound of formula I and its pharmacologically salts, esters and amides can be administered as a pure chemical, it is preferred that it be administered as a pharmaceutical composition. In either event, a contemplated compound is administered in an amount sufficient to provide a therapeutically effective dose, as is discussed hereinafter.

Accordingly, the present invention utilizes a pharmaceutical composition comprising a therapeutically effective dose of a compound of formula I or a pharmacologically acceptable salt, esters or amide thereof, hereinafter referred to as the "active ingredient" or "agent", dissolved or dispersed in a pharmacologically acceptable carrier or diluent.

A therapeutically effective amount of a contemplated chromone compound of formula I typically constitutes about 0.5 to about 10.0 weight percent of a contemplated composition. More preferably, that amount is about 2.0 to about 6.0 weight percent.

A pharmaceutical composition is prepared by any of the process well known in the art of pharmacy all of which involve bringing into association the active ingredient and the carrier therefore. For therapeutic use, a compound utilized in the present invention can be administered in the form of conventional pharmaceutical compositions. Such compositions can be formulated so as to be suitable for topical administration of the active ingredient. In these compositions, the agent is typically dissolved or dispersed in a physiologically tolerable carrier or diluent.

A carrier or diluent is a material useful for administering the active compound and must be "pharmacologically acceptable" in the sense of being compatible with the other ingredients of the composition and not deleterious to the recipient thereof. Thus, as used herein, the phrases "physiologically tolerable" and "pharmacologically acceptable" are used interchangeably and refer to molecular entities and compositions that do not produce an allergic or similar untoward reaction when administered to a human.

The pharmacologically tolerable carrier can take a wide variety of forms suitable for topical administration, such as an ointment, water-miscible ointment, cream, lotion, paste, gel or liniment. These carriers can be aqueous, oily (oleaginous) or water-miscible or water-dispersible. They can be oil-in-water or water-in-oil based emulsions. A discussion of some types of suitable carriers is present in U.S. Pat. No. 4,362,742, whose disclosures are incorporated herein by reference.

The preferred carrier composition for the disclosed process is an oil-in-water emulsion in which the active ingredient is present in the water phase. The preferred oil-in-water emulsion is comprised of a water phase containing the active ingredient. Water is typically present at about 40 to about 80 weight percent and more preferably at about 66 to about 72 weight percent of the composition.

One or more water-miscible organic solvents such as glycerine, propylene glycol can also be present in the water phase. A sequestering agent such as edetate disodium dihydrate (EDTA) can also be present, as can a pH value-adjusting acid. Phosphoric acid is also preferably used in the water phase in an amount required to obtain the required necessary pH value.

The pH value can range between about 3.2 and about 8.0. The more preferred pH value range is about 4.0 to about 7.0. The most preferred pH value is 5.5.

Compound names used herein are usually used common names as well as those utilized in the *International Cosmetic Ingredient Dictionary*, The Cosmetic, Toiletry, and Fragrance Association, Washington, D.C. (1993), and *The U.S. Pharmacopeia, The National Formulary*, [USP XXII; NF XVII] United States Pharmacopeial Convention, Inc., Rockville, Md., 1990.

The oil phase is comprised of materials that individually can be solids or liquids at room temperature, e.g. about 20°

C. These materials include waxes such as white wax and emulsifying wax, squalene and a silicone oil such as dimethicone. The oil phase also contains a component of the emulsifier, a $C_2$–$C_4$-acyl polypropyleneglycol (PPG) $C_{12}$–$C_{18}$ alkyl ether that contains an average of about 2–4 PPG groups per molecule. These materials impart an appropriate creamy feel to the composition upon the skin and tend to form an oleaginous layer over the treated uremic pruritus lesion.

A $C_{12}$–$C_{16}$ alcohol or mixtures thereof is also preferably present. Illustrative $C_{12}$–$C_{18}$ alcohols include lauryl, myristyl, cetyl, stearyl and oleyl alcohols.

The emulsifier includes emulsifying wax and preferably a mixture of two ingredients. The first is a $C_2$–$C_4$-acyl polypropyleneglycol (PPG) $C_{12}$–$C_{18}$ alkyl ether that contains an average of about 2–4 PPG groups per molecule. The second is a polyoxyethyleneglycol (PEG) $C_{14}$–$C_{26}$ ether having an average of about 8–12 PEG groups per molecule.

Emulsifying wax, and PEG compounds are preferably present together at about 8–17 weight percent of the total preparation, and in a weight ratio of about 15:1 to about 1:1, more preferably at about 10:1 to about 8:1, and most preferably about 9:1 in the order mentioned.

The ratio of the emulsifying wax and PEG emulsifier used is designed to provide a calculated HLB number of about 8 to about 14, and more preferably about 10 to about 12. The total amount of emulsifier used is typically a function of the total amount of oil phase ingredients, with more total emulsifier being used with a greater amount of oil phase ingredients, and less total emulsifier with the lower amount of oil phase ingredients, as is well known.

Emulsifying wax has an average HLB value of about 11. A particularly preferred PPG-containing emulsifier is PPG-2 myristyl ether propionate that has an HLB value of 11. A particularly preferred PEG-containing emulsifier is polyoxyethylene-10-oleyl ether that has an HLB value of 12.4. The above HLB value ranges are calculated based upon these emulsifiers.

PPG-2 myristyl ether propionate can be replaced with one of the compounds encompassed by the designation $C_2$–$C_4$ acyl-PPG(2–4) $C_{12}$–$C_{18}$ ether. Exemplary materials include PPG-3 lauryl ether butyrate and PPG-4 stearyl ether acetate, and the like. Similarly, PEG-10-oleyl ether (oleth-10; PEG compound) can be replaced with another PEG (7–12) $C_{14}$–$C_{20}$ alkyl ether such as PEG-12-cetyl ether (ceteth-12), PEG-7-stearyl ether (steareth-7), PEG-11-cetyl/stearyl ether (ceteareth-11), and the like.

It is noted that substitution in the PPG compound and PEG compound are considered together as these two compounds are present in the carrier in a combined total of 2–6 percent weight to weight with a weight to weight PPG-containing emulsifier to PEG-containing emulsifier ratio in the range of about 4:1–1:1, preferably about 3:1–2:1, most preferably of 2.5:1. This ratio results in the desired HLB number.

A contemplated preparation typically has a viscosity of a cream or ointment. Exemplary viscosities are thus about 20,000 to about 100,000 cps at 25° C., and more preferably about 50,000 to about 70,000 cps.

One and preferably more than one preservative is also preferably present in a commercial preparation. Exemplary preservatives include methylparaben, propylparaben and imidurea.

The following table provides a preferred range of weight to weight percentages for each particularly preferred ingredient present in a particularly preferred oil-in-water emulsion preparation for commercial use.

| Ingredient | % W/W Ranges |
| --- | --- |
| Cromolyn sodium | 0.5–10 |
| Emulsifying wax, N.F. | 8–17 total, in |
| Polyoxy-100 leyl Ether, N.F. | a ratio of |
| PPG-2 Myristyl Ether Propionate | 8:1–10:1 for the wax: PEG, and a 4:1–1:1 ratio for PPG: PEG |
| Squalene, U.S.P. | 2–10 |
| White Wax, N.F. | 0.5–5 |
| Dimethicone, N.F. | 0.5–5 |
| Cetyl Alcohol, N.F. | 1–10 |
| Propylparaben, N.F. | 0.05–0.2 |
| Purified Water, U.S.P. | q.s. |
| Glycerin, U.S.P. | 1–5 |
| Edetate Disodium Dihydrate, U.S.P. | 0.01–1.0 |
| Propylene Glycol, U.S.P. | 1–5 |
| Methylparaben, N.F. | 0.1–0.4 |
| Imidurea, N.F. | 0.1–0.3 |
| Phosphoric Acid, N.F. | q.s. |

Changes in the specific, particularly preferred, ingredients listed are contemplated. Thus, one of ordinary skill in the art can substitute similar ingredients for those discussed above without substantially altering the effectiveness of the carrier and the final composition. The viscosity of carrier can be changed so long as it remains suitable for topical application.

In addition, if a certain ingredient is changed resulting in different hydrophilic/lipophilic balance (HLB), this can be compensated for, using known techniques, by changing another ingredient.

Specific examples of the acceptable alterations in the particularly preferred given ingredients are set forth below. Specific combinations of changes that result in acceptable compositions are easily determined by known procedures because "acceptability" arises mostly from emulsion characteristics rather than from a major change in drug availability.

Dimethicone is a mixture of fully methylated linear siloxane polymers end-blocked with trimethylsiloxy units. These materials are commercially available from several suppliers at varying viscosities ranging from about 0.65 to about centistokes 2,500,000, (cSt), with lower molecular weight polymers exhibiting the lower viscosities up to about a weight of about 30,000 and viscosity of about 1000 cSt, at which polymer chain entanglement occurs, resulting in a leveling in properties.

A preferred dimethicone utilized herein has a viscosity of about 100 to about 300 cSt, and more preferably about 150 to about 250 cSt. [1 cSt=1 cps.]

Cetyl alcohol can be substituted by $C_{12}$–$C_{18}$ alkyl such as lauryl, myristyl, and stearyl alcohols. Methylparaben and propylparaben can be substituted by $C_1$–$C_5$ alkyl paraben, or other suitable preservatives.

Any pharmacologically suitable acid can be used in place of phosphoric acid to adjust the pH of the composition.

Other compounds that can be used in place of squalene include acelylated lanolin. Substitutions for imidurea include DMDM Hydantoin. Emulsifying wax can be replaced with cetyl alcohol: steareth-20 whereas stearamidopropyldimethyl amine can be used in place of white wax.

It should also be understood that in addition to the aforementioned carrier ingredients and substitutions, a pharmaceutical formulation described herein can include, as appropriate, one or more additional carrier ingredients such as buffers, binders, surface active agents, additional thickeners and preservatives (including antioxidants), lubricants, and the like. It is also contemplated that a penetration enhancer can be included to permit the active ingredient to penetrate the skin more effectively. One contemplated penetration enhancer is 2-n-nonyl-3-dioxolane, known as SEPA (Soft Enhancer for Percutaneous Absorption). SEPA can be used at about two weight percent (2 wt%) to about twenty weight percent (20 wt%). Fragrance and/or odor masking compounds can also be added.

C. Process

As noted earlier, a process for treating uremic pruritus is contemplated here. Broadly, a compound whose structure corresponds to that of formula I, or a pharmacologically acceptable salt, ester or amide thereof, as active ingredient, dissolved or dispersed in a pharmacologically acceptable carrier is topically administered (applied) to a pruritic lesion of a human patient. The compound is present in the composition in an amount sufficient to provide a therapeutically effective amount (a uremic pruritus lesion-reducing amount) of active ingredient compound over the period of administration. This amount ranges between about 0.02 g and about 0.4 g per treatment, and more preferably about 0.05 g to about 0.1 g per treatment. In severe cases, the therapeutically effective amount of active ingredient can range as high as about 1.2 g per treatment.

The composition is administered by topically applying the composition to an area affected by the uremic pruritus. The site can then be covered, or left open to the air. This treatment can be repeated a plurality of times such as several times per day for 12 months, or until the uremic pruritus regresses and disappears.

The duration of a particular treatment can vary depending upon the size, type and severity of the uremic pruritus. Typical administration lasts about 6 months. Administration is very easily carried out on an out-patient basis.

Efficacy of a contemplated process can be assessed by visual inspection of the patient's uremic pruritus lesion. The size and inflammation of the lesion typically begins to noticeably decrease after 2 weeks. Treatment is then continued until the lesion has disappeared.

EXAMPLE I

Exemplary Topical Preparation

A topical preparation for treating humans with uremic pruritus was prepared using the ingredients shown below for the preparation of 60 kilograms of 4.0 percent Cromolyn Sodium Cream:

| Ingredient | % W/W |
| --- | --- |
| Cromolyn sodium | 4.00 |
| Emulsifying wax, N.F. | 9.00 |
| PPG-2 Myristyl Ether Propionate | 2.50 |
| Polyoxy-10-Oleyl Ether, N.F. | 1.00 |
| Squalene, U.S.P. | 4.00 |
| White Wax, N.F. | 2.00 |
| Dimethicone, N.F. | 1.00 |
| Cetyl Alcohol, N.F. | 3.00 |
| Propylparaben, N.F. | 0.10 |
| Purified Water, U.S.P. | 68.80 |
| Glycerin, U.S.P. | 2.50 |
| Edetate Disodium Dihydrate, U.S.P. | 0.10 |
| Propylene Glycol, U.S.P. | 1.50 |
| Methylparaben, N.F. | 0.20 |
| Imidurea, N.F. | 0.30 |
| Phosphoric Acid, N.F. | q.s |
| pH value | 5.5 |
| Viscosity (25° C.) | 60,000cps |

This cream is prepared by the following procedure. Percentage of total weight is given in parenthesis.

Step 1. Charge the main mixing kettle with 25.68K of purified water (42.80%) and heat to 75°–80° C. Add 1.50K of glycerin (2.50%), 60 g of disodium EDTA U.S.P. (0.10%) and 900 g of propylene glycol (1.50%) individually while mixing at 30 rpm. Add 120 g of methylparaben N.F. (0.20%) and mix for 5 minutes at 30 rpm to disperse. Reduce speed to 20 rpm and mix for ½ hour.

Step 2. In a separate container, heat 5.40K of emulsifying wax N.F. (9.00%), 1.50K of PPG-2 myristyl ether propionate (2.50%), 600 g polyoxy-10 oleyl ether N.F. (1.00%), 2.40K squalene U.S.P. (4.00%), 1.20K white wax (2.00%), 600 g dimethicone N.F. (1.00%), 1.80K cetyl alcohol (3.00%) and 60 g propylparaben N.F. (0.10%) to 75°–80° C. Mix at 1700 rpm for 5 minutes.

Step 3. At 75°–80° C., add Step #2 to Step #1 with mixing at 40 rpm. Mix at 40 rpm speed for ½ hour.

Step 4. Cool evenly to 35°–40° C. over a 60 minute period with mixer at 20 rpm.

Step 5. Premix 600 g of purified water U.S.P. (1.00%) and 180 g of imidurea N.F. (0.30%) in a separate container at 250 rpm on the Dayton Gearmixer. Mix manually for 15 minutes. This premix phase should be totally clear before addition to the batch.

Step 6. Add the mixture from step #5 to that at Step #4 and mix well for 10 minutes at 10 rpm.

Step 7. In a separate container premix 15.00K of purified water (25.00%) and 2.40K of cromolyn sodium U.S.P. (4.00%) using the Lightnin' mixer at 1750 rpm for 20 minutes and check for uniformity.

Step 8. Add the contents of step #7 to the batch and mix for ½ hour at 20 rpm.

Step 9. Adjust pH to 5.5 with phosphoric acid N.F. if necessary.

Two sets of samples from the top, middle and bottom of the kettle are removed and submitted for cromolyn sodium, methylparaben and propylparaben analysis and other physical tests.

EXAMPLE II

Clinical Trial

A Clinical Trial of the claimed and described process, using the claimed and described composition has been initiated. The trial involves a 13-month double-blind cross-over study period, with a 1-month observation period, followed by 3 months of treatment, 3 months without treatment, 3 months of treatment and 3 months without treatment. The subjects will be evaluated based on measurement of itch and lesion reduction. No data are currently available.

The foregoing description is intended as illustrative and is not to be taken as limiting. Still other variations within the spirit and scope of this invention are possible and will readily present themselves to those skilled in the art.

I claim:

1. A process for treatment of uremic pruritus in humans comprising topically administering to the pruritic lesion of said human a composition of a pharmacologically acceptable carrier having dissolved or dispersed therein a therapeutically effective amount of a substituted chromone compound or a pharmacologically acceptable salt, ester or amide thereof, said chromone compound having a structure represented by the formula:

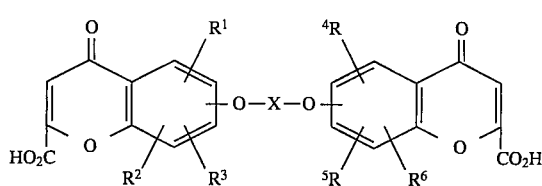

wherein
- (a) $R^1$, $R^2$, $R^3$, $R^4$, $R^5$, and $R^6$ can each be the same, or different, and each R group is selected from the group consisting of hydrogen, a halo group, a $C_1$–$C_6$ lower alkyl group, hydroxyl, $C_1$–$C_6$ lower alkoxy, substituted $C_1$–$C_6$ lower alkoxy group, and a substituted $C_1$–$C_6$ lower alkyl, where the substituent is selected from the group consisting of a hydroxyl, a lower ($C_1$–$C_6$) alkoxy group, a carboxy group, a halo group, a lower alkenyl group, a benzyl group and nitro group;
- (b) the X group can be a straight or branched, saturated or unsaturated hydrocarbon chain having between 3 and 10 carbon atom, whose hydrocarbon chain can be interrupted by a substituent selected from the group consisting of oxygen, a carbonyl group, a carbocyclic or heterocyclic ring and can contain a substituent selected from the group consisting of a halo group, a hydroxyl group, and a $C_1$–$C_6$ lower alkoxy group.

2. The process of claim 1 wherein no more than one of said $R^1$, $R^2$ and $R^3$ and no more than one of said $R^4$, $R^5$ and $R^6$ is other than hydrogen wherein each said $R^1$–$R^6$ is unsubstituted; and wherein X is a straight or branched hydrocarbon chain that contains 3–7 carbon atoms.

3. The process of claim 1 wherein each of said $R^1$, $R^2$, $R^3$, $R^4$, $R^5$, and $R^6$ is hydrogen and said carboxyl groups are present as alkali metal carboxylate salts.

4. The process of claim 3 wherein X is a polymethylene chain substituted by one or more hydroxyl groups.

5. The process of claim 1 wherein said carrier contains a penetration enhancer to aid in absorption by the skin of said substituted chromone compound.

6. The process of claim 1 wherein said administration is repeated a plurality of times.

7. A process for treatment of uremic pruritus in humans comprising topically administering a therapeutically effective amount of the compound, 1,3-bis(2-carboxychromon-5-yloxy)-2-hydroxypropane, or a pharmacologically acceptable salt, ester or amide thereof, dissolved or dispersed in a pharmacologically acceptable carrier to the pruritic lesion of said human.

8. The process of claim 7 wherein said compound is administered in an amount of about 40 to about 3600 milligrams per day.

9. The process of claim 7 wherein said administration is repeated a plurality of times.

10. The process of claim 7 wherein said compound is administered in an amount of about 100 to about 500 milligrams per day.

11. The process of claim 7 wherein said carrier contains a penetration enhancer to aid in absorption, by the skin, of said compound.

* * * * *